United States Patent
Hino et al.

(10) Patent No.: US 6,740,318 B2
(45) Date of Patent: May 25, 2004

(54) ADDITIVE FOR HAIR GROWING AGENT AND HAIR GROWING AGENT COMPOSITION

(75) Inventors: Takakazu Hino, Yokohama (JP); Isao Noda, Yokosuka (JP)

(73) Assignee: Nippon Unicar Company Limited, Tokyo (JP)

( * ) Notice: Subject to any disclaimer, the term of this patent is extended or adjusted under 35 U.S.C. 154(b) by 30 days.

(21) Appl. No.: 09/877,257

(22) Filed: Jun. 11, 2001

(65) Prior Publication Data

US 2003/0003072 A1 Jan. 2, 2003

(51) Int. Cl.$^7$ .................................. A61K 7/06
(52) U.S. Cl. ............... 424/70.1; 424/70.16; 424/70.12; 556/445; 556/446
(58) Field of Search ............... 424/70.1, 70.11, 424/70.12; 556/445, 446

(56) References Cited

U.S. PATENT DOCUMENTS

| | | | | |
|---|---|---|---|---|
| 4,139,619 A | | 2/1979 | Chidsey, III ................ | 424/45 |
| 4,378,345 A | * | 3/1983 | Okumura et al. ............ | 424/45 |
| 4,978,681 A | * | 12/1990 | Adachi et al. ............... | 514/557 |
| 5,472,686 A | * | 12/1995 | Tsubaki et al. .............. | 424/59 |
| 6,051,730 A | * | 4/2000 | Pallas et al. ................. | 504/101 |
| 6,255,313 B1 | | 7/2001 | Suzuki et al. ............... | 514/272 |
| 6,380,263 B1 | | 4/2002 | Pruche et al. ............... | 514/880 |

FOREIGN PATENT DOCUMENTS

EP          1 050 310          11/2000

* cited by examiner

Primary Examiner—Thurman K. Page
Assistant Examiner—Lakshmi Channavajjala
(74) Attorney, Agent, or Firm—Westerman, Hattori, Daniels & Adrian, LLP

(57) ABSTRACT

A hair growing agent composition containing a pharmaceutically active component, solvent and the additive shown by the following formula (I) or (II)

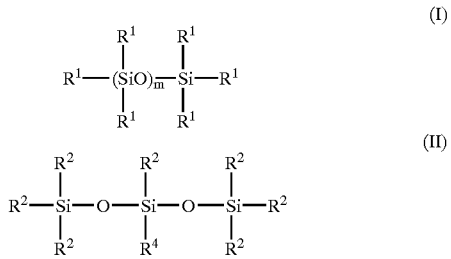

wherein, $R^1$ is an alkyl group having a carbon number of 1 to 30, an aryl group or a group shown by the formula $(R^2)_3SiO-$ or $-YO(C_2H_4O)_a(C_3H_6O)_bR^3$; at least one $R^1$s is an alkyl group having a carbon number of 6 to 30 or a group shown by the formula $-YO(C_2H_4O)_a(C_3H_6O)_bR^3$; $R^2$ is an alkyl group having a carbon number of 1 to 5 or an aryl group; $R^3$ is a hydrogen, an alkyl group having a carbon number of 1 to 6 or an acetoxy group; Y is a divalent organic group bound to an adjacent silicon atom through a carbon-silicon bond and to a polyoxyalkylene block through an oxygen atom; $R^4$ is an alkyl group having a carbon number of 6 to 30 or a group shown by the formula $-YO(C_2H_4O)_a(C_3H_6O)_bR^3$; m is 1 to 50: and a and b are 0 to 50 respectively and satisfy the relationship $a+b \geq 2$.

1 Claim, No Drawings

ADDITIVE FOR HAIR GROWING AGENT AND HAIR GROWING AGENT COMPOSITION

TECHNICAL FIELD OF THE INVENTION

This invention relates to an additive for hair growing agent and a hair growing agent composition containing it, more particularly it relates to the additive for hair growing agent composed of a specific silicone-based compound and capable to secure the hair growing effect, even if the content of the pharmaceutically active components is reduced from that of the conventional hair growing agent composition, hence the side-effect thereof could be reduced, and to the hair growing agent composition containing it.

BACKGROUND OF THE INVENTION

Hair growing agents incorporated with a variety of pharmaceutically active components have been known and widely used to remove or reduce the causes for baldness or loss of hair. However, many of these pharmaceutically active components have potential risk to produce side-effects. For example, minoxidil (2,4-diamino-6-piperidinopyrimidine-3-oxide), which recently has been widely used, is a pharmaceutical originally developed as a remedy for hypertension, and will cause the problem, when used as the hair growing agent, by the antihypertensive action of the minoxidil due to its original pharmaceutical effect.

SUMMARY OF THE INVENTION

It is an object of this invention to offer an inexpensive hair growing agent composition which has a low potential of the side-effect by decreasing the content of the pharmaceutically active components, while keeping the sufficient hair growing effect.

DISCLOSURE OF THE INVENTION

The inventors of the present invention have found, after having extensively studied to solve the above problem, that a hair growing agent composition can exhibit a sufficient hair growing action, even when the content of the pharmaceutically active components is decreased, by incorporating a silicone-based compound of the specific structure therein, and this invention has been accomplished basing on the above knowledge.

This invention offers an additive for hair growing agent shown by the following general formula (I):

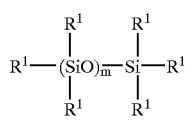
(I)

wherein, $R^1$ is an alkyl group having a carbon number of 1 to 30, an aryl group or a group shown by the formula $(R^2)_3SiO$— or —$YO(C_2H_4O)_a(C_3H_6O)_bR^3$; at least one of $R^1$s is an alkyl group having a carbon number of 6 to 30 or a group shown by the formula —$YO(C_2H_4O)_a(C_3H_6O)_bR^3$; $R^2$ is an alkyl group having a carbon number of 1 to 5 or an aryl group; $R^3$ is a hydrogen atom, an alkyl group having a carbon number of 1 to 6 or an acetoxy group; Y is a divalent organic group bound to an adjacent silicon atom through a carbon-silicon bond and to a polyoxyalkylene block through an oxygen atom; m is a number of 1 to 50 on the average; and a and b are numbers of 0 to 50 on the average respectively, but they satisfy the relationship $a+b \geq 2$.

This invention also offers an additive for hair growing agent shown by the following general formula (II):

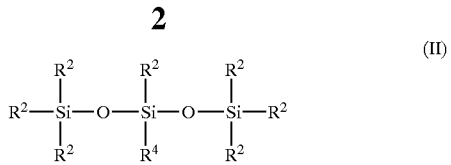
(II)

wherein, $R^4$ is an alkyl group having a carbon number of 6 to 30 or a group shown by the formula —$YO(C_2H_4O)_a(C_3H_6O)_bR^3$; and $R^2$, $R^3$, Y, a and b are the same as those defined in the general formula (I).

This invention also offers a hair growing agent composition containing a pharmaceutically active component, solvent and the additive for hair growing agent shown by the general formula (I) or (II).

PREFERRED EMBODIMENTS OF THE INVENTION

This invention is described more concretely.

The additive for hair growing agent of this invention is a compound shown by the following general formula (I):

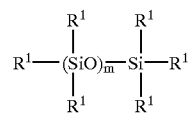
(I)

wherein, $R^1$ is an alkyl group having a carbon number of 1 to 30, an aryl group or a group shown by the formula $(R^2)_3SiO$— or —$YO(C_2H_4O)_a(C_3H_6O)_bR^3$; at least one of $R^1$s is an alkyl group having a carbon number of 6 to 30 or a group shown by the formula —$YO(C_2H_4O)_a(C_3H_6O)_bR^3$; $R^2$ is an alkyl group having a carbon number of 1 to 5 or an aryl group; $R^3$ is a hydrogen atom, an alkyl group having a carbon number of 1 to 6 or an acetoxy group; Y is a divalent organic group bound to an adjacent silicon atom through a carbon-silicon bond and to a polyoxyalkylene block through an oxygen atom; m is a number of 1 to 50 on the average; and a and b are numbers of 0 to 50 on the average respectively, but they satisfy the relationship $a+b \geq 2$.

It is essential that at least one of $R^1$s in the general formula (I) is an alkyl group having a carbon number of 6 to 30 or a group shown by the formula —$YO(C_2H_4O)_a(C_3H_6O)_bR^3$, and the remainder is preferably methyl, ethyl or phenyl group, or a group shown by the formula $(R^2)_3SiO$—, more preferably methyl group or a group shown by the formula $(CH_3)_3SiO$—.

$R^2$ is an alkyl group having a carbon number of 1 to 5 or an aryl group, preferably an alkyl group having a carbon number of 1 to 3, more preferably methyl group.

$R^3$ is a hydrogen atom, an alkyl group having a carbon number of 1 to 6 or an acetoxy group, preferably a hydrogen atom, or methyl or butyl group.

The preferable examples of Y include —$CH_2CH_2CH_2$— and —$CH_2CH(CH_3)CH_2$—, the former being more preferable.

It is essential that m is a number of 1 to 50 on the average, preferably 1 to 5.

It is essential that a and b are numbers of 0 to 50 on the average respectively and they satisfy the relationship $a+b \geq 2$, and it is preferable that a is 2 to 20 and b is 0 to 10.

Among the compounds shown by the general formula (I), the particularly preferable one is shown by the following general formula (II):

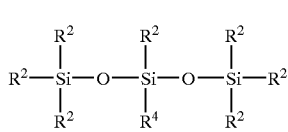
(II)

wherein, $R^4$ is an alkyl group having a carbon number of 6 to 30 or a group shown by the formula $-YO(C_2H_4O)_a(C_3H_6O)_bR^3$; and $R^2$, $R^3$, Y, a and b are the same as those defined in the general formula (I).

The concrete examples of the preferable compounds include Compounds 1 to 3 shown by the following general formulae:

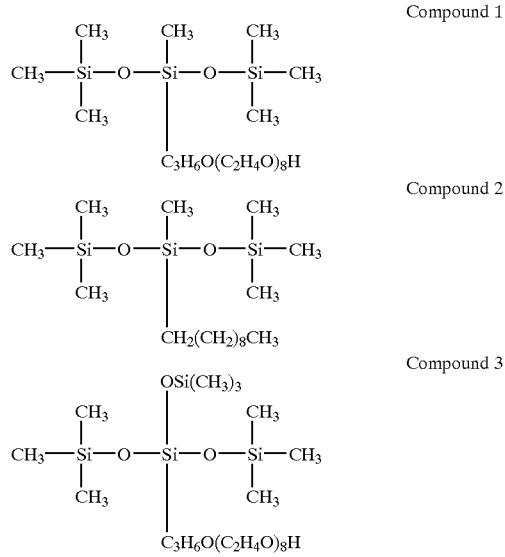

When incorporated in a hair growing agent, the additive for hair growing agent of this invention can decrease the content of the pharmaceutically active component. The hair growing agent in which the additive of this invention is incorporated is not limited, and any known one may be used. A hair growing agent generally comprises a pharmaceutically active component, solvent and additives.

The pharmaceutically active components useful for this invention include vasodilator (e.g., minoxidil, carpronium chloride, benzyl nicotinate, Swertia japonica extract, panax ginseng extract, vitamin E acetate or capsicum tincture), antihistamic agent (diphenhydramine hydrochloride or isothipendyl hydrochloride), antiinflammatory agent (glycyrrhizinic acid or guaiazulene), keratin-dissolving agent (e.g., urea or salicylic acid), antimicrobial agent (chlorhexidine gluconate, isopropyl methylphenol, quarternary ammonium salt, hinokitiol or piroctone olamine), humectant (e.g., sodium hyaluronate or chondroitin sulfate), extracts of various plants or animals (e.g., yew, *Paeonia suffruticosa* Andrews, Licorice, St. John's Wort, Aconiti Tuber, Loquat, *Artemisia capillaris*, comfrey, *Angelica keiskei*, saffron, gardeniae Fructus, rosemary, sage, *Saussurea lappa* Clarke, *Vladimiria denticulata* Ling, hop or placenta), and vitamin (e.g., retinol acetate, pyridoxine hydrochloride, ascorbic acid, thiamine nitrate, cyanocobalamin or biotin).

The solvents useful for this invention include water, alcohols (methanol, ethanol, 2-propanol or denatured ethanol), and cyclosiloxanes (e.g., decamethylcyclopentasiloxane), of which water, ethanol or 2-propanol is preferable.

Other additives useful for this invention include those normally used, such as an antioxidant (e.g., dibutyl hydroxytoluene, sodium pyrosulfite, tocopherol, sodium edetate, ascorbic acid or isopropyl gallate), solubilizer (e.g., diisopropyl adipate, isopropyl myristate, polyethylene glycol, medium chain fatty acid triglyceride, fatty acid ester, various vegetable oils, various animal oils, polyhydric alcohol/fatty acid ester, alkyl glyceryl ether, hydrocarbon, lactic acid or sodium hydroxide), metabolism activator (e.g., panthenol), surfactant (e.g., sorbitan/fatty acid ester, glycerin/fatty acid ester, polyglycerin/fatty acid ester, propylene glycol/fatty acid ester, polyoxyethylene sorbitan/fatty acid ester, polyoxyethylene sorbit/fatty acid ester, polyoxyethylene glycerin/fatty acid ester, polyoxyethylene glycol/fatty acid ester, polyoxyethylene alkyl ether, polyoxyethylene polyoxypropylene alkyl ether, polyoxyethylene alkyl phenyl ether, polyoxyethylene hydrogenated castor oil, polyoxyethylene castor oil, polyoxyethylene beeswax derivative, polyoxyethylene lanolin derivative, polyoxyethylene alkyl amide, polyoxyethylene alkyl amine, lecithin derivative or high-molecular-weight emulsifier), emulsion stabilizer (e.g., higher alcohol), gelling agent (water-soluble high-molecular-weight compound), adhesive, perfume, refrigerant (e.g., menthol, peppermint oil or camphor), or dyestuffs, which may be used within limits where the effect of this invention is not interfered.

The content of the additive for the hair growing agent of this invention is not limited, but preferably it is 0.01 to 2% by weight, more preferably 0.02 to 0.2% by weight, in the hair growing agent composition.

The method for incorporating the additive for the hair growing agent of this invention is not limited, and it may be made by mixing in conventional manners. It may be added to the hair growing agent directly or after being dissolved in a solvent. The solvent may be one described earlier as one of the components for the hair growing agent. The commercial hair growing agent is designed to have a storage stability, and thus the addition of the additive for the hair growing agent of this invention may deteriorate the stability. Therefore, the additive for the hair growing agent of this invention or a solution thereof may be added to the hair growing agent immediately before it is used.

The hair growing agent composition comprising the above-described pharmaceutically active component, solvent, additive for the hair growing agent of this invention, and, as required, one or more other additives is one of the embodiments of this invention.

The content of the pharmaceutically active component varies depending on its type. For example, minoxidil is incorporated preferably at 0.05 to 2% by weight, and carpronium chloride, preferably at 0.25 to 2% by weight. The preferable content of the additive for the hair growing agent of this invention is these range described.

The mechanism of the additive for the hair growing agent of this invention is not fully understood. It is however considered that it easily penetrates into very narrow gaps between the hair roots and hair follicles, which, coupled with the percutaneous absorption from the scalp on which the conventional one depends, allows the additive to directly reach the hair papillas, with the result that the pharmaceutically active component efficiently works on the hair papillas and hence sufficiently exhibits its effect even at the decreased content.

EXAMPLES

This invention is described more concretely by Examples, which by no means limit this invention, and variations may be made without departing from the spirit and scope of the invention.

Preparation of the Hair Growing Agent Composition

Lotion type preparations for external use were prepared by mixing and dissolving minoxidil, the additive for the hair growing agent, 30 ml ethanol and sufficient purified water to make 100 ml in total as shown their composition in Table 1.

Trichogenous Test.

Groups of $C_3H$-based mice (male, 7 weeks old), each consisting of 10 mice, were subjected to the trichogenous test, where each composition shown in Table 1 was applied at 0.2 ml a day for 20 days to each group of the mice at the 2 by 3 cm area on the back, after hair of that area was cut by hair clippers.

The body hair of the tested animal is black, and the hair-free skin is brown. The hair turns from gray to black in color tone as it grows. Therefore, extent of blackness of the body hair was evaluated by visual observation according to six-grade system; 0: no hair was observed to grow, 1: hair was observed to grow, 2: terminal hair was neatly grown, 3: terminal hair was grown to approximately 50% of the normal, 4: terminal hair was grown to approximately 70% of the normal, and 5: terminal hair was grown to approximately 100% of the normal. The results are given in Table 1.

TABLE 1

| Compositions (unit: g) | Comparative Example 1 | Comparative Example 2 | Comparative Example 3 | Example 1 | Example 2 | Example 3 |
|---|---|---|---|---|---|---|
| (A) Pharmaceutically active component Minoxidil | 1.0 | 0.5 | 0.3 | 0.5 | 0.3 | 0.5 |
| (B) Solvent | Sufficient | Sufficient | Sufficient | Sufficient | Sufficient | Sufficient |
| Purified water | purified water to make 100 ml in total | purified water to make 100 ml in total | purified water to make 100 ml in total | purified water to make 100 ml in total | purified water to make 100 ml in total | purified water to make 100 ml in total |
| Anhydrous ethanol | 30.00 | 30.00 | 30.00 | 30.00 | 30.00 | 30.00 |
| (C) Additive for hair growing agent | | | | | | |
| Compound 1 | — | — | — | 0.05 | 0.05 | — |
| Compound 2 | — | — | — | — | — | 0.05 |
| Hair-growing effect | 5 | 3 | 0 | 5 | 5 | 5 |

It is confirmed, as shown in Table 1, that the hair growing agent composition incorporated with the additive for the hair growing agent of this invention has significant hair growing effect at a lower content of the pharmaceutically active component than the one in which of the additive is not incorporated.

As described above, the additive for the hair growing agent of this invention brings about an advantage of allowing the hair growing agent incorporated therewith to secure a sufficient hair growing effect even at a lower content of the pharmaceutically active component than that for the conventional one. Therefore, the additive for the hair growing agent of this invention and hair growing composition incorporated therewith are industrially very useful.

What is claimed is:

1. A hair growing agent composition containing a pharmaceutically active component, solvent and an additive for hair growing agent show by formula (II) below:

$$R^2-\underset{\underset{R^2}{|}}{\overset{\overset{R^2}{|}}{Si}}-O-\underset{\underset{R^4}{|}}{\overset{\overset{R^2}{|}}{Si}}-O-\underset{\underset{R^2}{|}}{\overset{\overset{R^2}{|}}{Si}}-R^2 \qquad (II)$$

wherein, $R^2$ is an alkyl group having a carbon number of 1 to 5 or an aryl group; $R^4$ is an alkyl group having a carbon number of 6 to 30 or a group shown by the formula $-YO(C_2H_4O)_a(C_3H_6O)_bR^3$; $R^3$ is hydrogen, an alkyl group having a carbon number of 1 to 6 or an acetoxy group; Y is a divalent organic group bound to an adjacent silicon atom through a carbon-silicon bond and to a polyoxyalkylene block through an oxygen atom; and a and b are 0 to 50 respectively and satisfy the relationship $a+b \geq 2$ wherein said hair growth additive is present in an amount sufficient to increase the hair growing effect of the hair growing agent.

\* \* \* \* \*